(12) United States Patent
Afilani

(10) Patent No.: US 11,300,541 B2
(45) Date of Patent: Apr. 12, 2022

(54) DYNAMIC SELECTIVE POLARIZATION MATCHING FOR REMOTE DETECTION OF SMOKELESS GUNPOWDER

(71) Applicant: DKL INTERNATIONAL, INC., Fernandina Beach, FL (US)

(72) Inventor: Thomas L. Afilani, Jersey Shore, PA (US)

(73) Assignee: DKL INTERNATIONAL, INC., Fernandina Beach, FL (US)

(*) Notice: Subject to any disclaimer, the term of this patent is extended or adjusted under 35 U.S.C. 154(b) by 245 days.

(21) Appl. No.: 16/797,136

(22) Filed: Feb. 21, 2020

(65) Prior Publication Data

US 2020/0191747 A1 Jun. 18, 2020

Related U.S. Application Data

(63) Continuation-in-part of application No. 16/524,672, filed on Jul. 29, 2019.

(60) Provisional application No. 62/713,233, filed on Aug. 1, 2018.

(51) Int. Cl.
*G01N 27/60* (2006.01)
*G01N 33/00* (2006.01)

(52) U.S. Cl.
CPC ......... *G01N 27/60* (2013.01); *G01N 33/0057* (2013.01)

(58) Field of Classification Search
CPC ............................ G01N 27/60; G01N 33/0057
USPC ....................................................... 324/454
See application file for complete search history.

(56) References Cited

U.S. PATENT DOCUMENTS

| 5,019,804 | A | * | 5/1991 | Fraden | G08B 13/26 327/509 |
| 5,652,577 | A | * | 7/1997 | Frasier | G08G 1/042 324/236 |
| 5,748,088 | A | | 5/1998 | Afilani | |
| 5,907,280 | A | | 5/1999 | Afilani | |
| 6,011,476 | A | | 1/2000 | Afilani | |
| 6,078,179 | A | * | 6/2000 | Afilani | G01N 27/60 324/452 |
| 6,346,865 | B1 | | 2/2002 | Maynord et al. | |

(Continued)

FOREIGN PATENT DOCUMENTS

WO         WO 98/48267        10/1998

OTHER PUBLICATIONS

International Search Report dated Oct. 17, 2019 issued in PCT International Patent Application No. PCT/US2019/043885, 4 pp.

(Continued)

*Primary Examiner* — Christopher P McAndrew
(74) *Attorney, Agent, or Firm* — Nixon & Vanderhye P.C.

(57) ABSTRACT

An analog matching filter includes a first plate, a second plate coupled with the first plate and separated from the first plate via a spacer, and a replicate matching material fixed to an inside surface of the first plate. A conductive plate or sheet is fixed to an inside surface of the second plate. An electrical circuit connects the first plate to the conductive plate or sheet. The replicate matching material and the conductive plate or sheet generate an opposite polarization pattern carried by the electrical circuit that is based on a polarization pattern of smokeless gunpowder according to a spatial gradient of the smokeless gunpowder local electric field distribution.

20 Claims, 5 Drawing Sheets

(56) References Cited

U.S. PATENT DOCUMENTS

| | | | |
|---|---|---|---|
| 6,407,556 B1* | 6/2002 | Rudeke | G08B 13/26 |
| | | | 324/663 |
| 6,411,099 B1* | 6/2002 | Afilani | G01N 27/60 |
| | | | 324/452 |
| 6,496,114 B1 | 12/2002 | Afilani | |
| 6,674,366 B1 | 1/2004 | Afilani | |
| 6,686,842 B1 | 2/2004 | Afilani | |
| 7,410,612 B1* | 8/2008 | Carrington | G01N 31/22 |
| | | | 422/531 |
| 7,705,611 B2* | 4/2010 | Ogata | H03K 17/955 |
| | | | 324/661 |
| 10,816,456 B2 | 10/2020 | de Oliveira Botelho | |
| 2004/0114130 A1 | 6/2004 | Nguyen | |
| 2013/0228474 A1 | 9/2013 | Sloss et al. | |
| 2015/0233795 A1* | 8/2015 | Glattstein | G01N 1/2202 |
| | | | 436/165 |
| 2015/0293048 A1* | 10/2015 | Wang | G01N 33/0057 |
| | | | 205/790.5 |
| 2018/0106759 A1 | 4/2018 | de Oliveira Botelho | |
| 2022/0026478 A1 | 1/2022 | Afilani | |

OTHER PUBLICATIONS

Senesac, Larry et al., "Nanosensors for Trace Explosive Detection," Materials Today, vol. 11, No. 3, Mar. 2008, pp. 28-36.
Wasisto, Hutomo Suryo et al., "Airborne Engineered Nanoparticle Mass Sensor Based on a Silicon Resonant Cantilever," Sensors and Actuators B: Chemical 180 (2013), pp. 77-89.

* cited by examiner

DYNAMIC SELECTIVE POLARIZATION MATCHING FOR REMOTE DETECTION OF SMOKELESS GUNPOWDER

CROSS-REFERENCES TO RELATED APPLICATIONS

This application is a continuation-in-part of U.S. patent application Ser. No. 16/524,672, filed Jul. 29, 2019, which claims the benefit of U.S. Provisional Patent Application No. 62/713,233, filed Aug. 1, 2018, the entire contents of each of which are herein incorporated by reference.

STATEMENT REGARDING FEDERALLY SPONSORED RESEARCH OR DEVELOPMENT (NOT APPLICABLE)

BACKGROUND

The invention relates to investigating or analyzing materials or entities of interest by the use of electric, electrochemical, or magnetic means by investigating electrostatic variables. More specifically, the invention uses the fields of electrostatics and dielectrokinesis (phoresis) with electronics to engage the analog matching filter for the purpose of detection of a variety of specific materials and compositions of matter including smokeless gunpowder. The invention is suitable for use with products manufactured by DrawDown Detection Inc.

In recent years, advances in technology, internet, 3D printing, and communications have provided individuals the ability to create weapons using a variety of specific materials and compositions of matter, including smokeless gunpowder that are difficult to detect using traditional detectors and scanners. This has created a void in the ability to maintain the highest level of security for schools, office buildings, and other public and private areas. In the Oct. 1, 2017 Las Vegas shooting, a hotel room was used to store large amounts of ammunition that were subsequently used to kill 58 people and wound 422, with the ensuing panic bringing the injury total to 851. A capability to detect the smokeless gunpowder carried to or stored in the hotel room could have prevented this type of killing spree The capability to detect smokeless gunpowder used on "soft targets" as a weapon of mass terror is an unmet need worldwide. Current capabilities such as search dogs, trace detection and physical inspections are effective when used at controlled check points. However, these capabilities are not effective for Standoff detection. The loaded guns and stored ammunition such as used in the 2017 Las Vegas Hotel shooting or other mass shootings require standoff detection.

BRIEF SUMMARY

Standoff sensors capable of locating from a distance would be an effective tool for public and private security and safety professionals. A widely deployed hand-held standoff sensor capable of alerting to the presence and location of smokeless gunpowder could enable first responders to interdict, deactivate or isolate before an attack. Standoff detection would also provide deterrence wherever the sensor was available.

Standoff sensors operate in the ULF (near DC) frequency. The Standoff Sensor of the described embodiments is passive and emits no detectable emissions. The Sensor acts as a transducer that converts electric field energy into a force aligning an internal member to the source of the electric field. Location information is displayed digitally. The Sensor employs an RC (capacitors and resistors) circuit and an impedance-matching filter circuit with bandpass frequency filtering in the ULF range.

Discriminatory detection of the target electric field is achieved by the selective relative permittivity of the capacitive elements of the detection circuit. The permittivity of the replicate property dielectric material and the configuration of the capacitive elements define the dielectric strength or minimum electric field for the detection.

Permittivity transmits (or "permits") an electric field to charge the analog matching filter of the described embodiments and allows electric field charge to be stored and converted to a dielectrokinesis (phoresis) force. The selective permittivity is arranged in an analog matching filter in an RC circuit that enables the electric field stored charge to be converted to the dielectrokinesis (phoresis) force and enabling the detection.

In an exemplary embodiment, an analog matching filter includes a first plate, a second plate coupled with the first plate and separated from the first plate via a spacer, a replicate matching material fixed to an inside surface of the first plate, and a conductive plate or sheet fixed to an inside surface of the second plate. An electrical circuit connects the first plate to the conductive plate or sheet. The replicate matching material and the conductive plate or sheet generate an opposite polarization pattern carried by the electrical circuit that is based on a polarization pattern of smokeless gunpowder according to a spatial gradient of the smokeless gunpowder local electric field distribution.

The replicate may be configured to perform a spatial dielectric property matching of the smokeless gunpowder. The replicate matching material may be selected in accordance with dielectric polarization characteristics of the smokeless gunpowder. The replicate matching material may include one or more dielectric materials. The replicate matching material may include smokeless gunpowder. The replicate matching material may include identical dielectric properties, time constants and related macroscopic friction coefficients to those of the smokeless gunpowder. The replicate matching material may include compositions of nitrated cellulose and nitroglycerin.

In another exemplary embodiment, a sensor device for detecting smokeless gunpowder includes a housing, a first analog matching filter and a second analog matching filter. Each of the first and second analog matching filters includes a first plate, a second plate coupled with the first plate and separated from the first plate via a spacer, a replicate matching material fixed to an inside surface of the first plate, and a conductive plate or sheet fixed to an inside surface of the second plate. An electrical circuit connects the first plate to the conductive plate or sheet. The sensor device also includes an internal member that is configured to react to the opposite polarization pattern carried by the electrical circuit, and a switch coupled with the first and second analog matching filters that selectively activates the first analog matching filter or the second analog matching filter. The replicate matching material and the conductive plate or sheet in at least the first analog matching filter generates an opposite polarization pattern carried by the electrical circuit that is based on a polarization pattern of smokeless gunpowder according to a spatial gradient of the smokeless gunpowder local electric field distribution.

The replicate matching material of the first analog matching filter may be different from the replicate matching material of the second analog matching filter.

In yet another exemplary embodiment, a method of detecting smokeless gunpowder from a distance using the sensor of the described embodiments includes the steps of (a) moving the sensor in a first direction; (b) immediately after step (a), moving the sensor in a second direction, opposite from the first direction, wherein steps (a) and (b) cause the sensor to pass through unique electric field spatial gradients of the smokeless gunpowder; and (c) using a selective permittivity via the replicate matching material to enable the opposite polarization pattern to be converted to a dielectrokinesis (phoresis) force based on a presence of the smokeless gunpowder. Steps (a) and (b) may be practiced with the sensor in an essentially horizontal orientation. Steps (a) and (b) may be practiced across an essentially horizontal plane. The method may also include, after step (c), driving a display based on the dielectrokinesis (phoresis) force.

BRIEF DESCRIPTION OF THE DRAWINGS

These and other aspects and advantages will be described in detail with reference to the accompanying drawings, in which.

DETAILED DESCRIPTION

Figure 1:
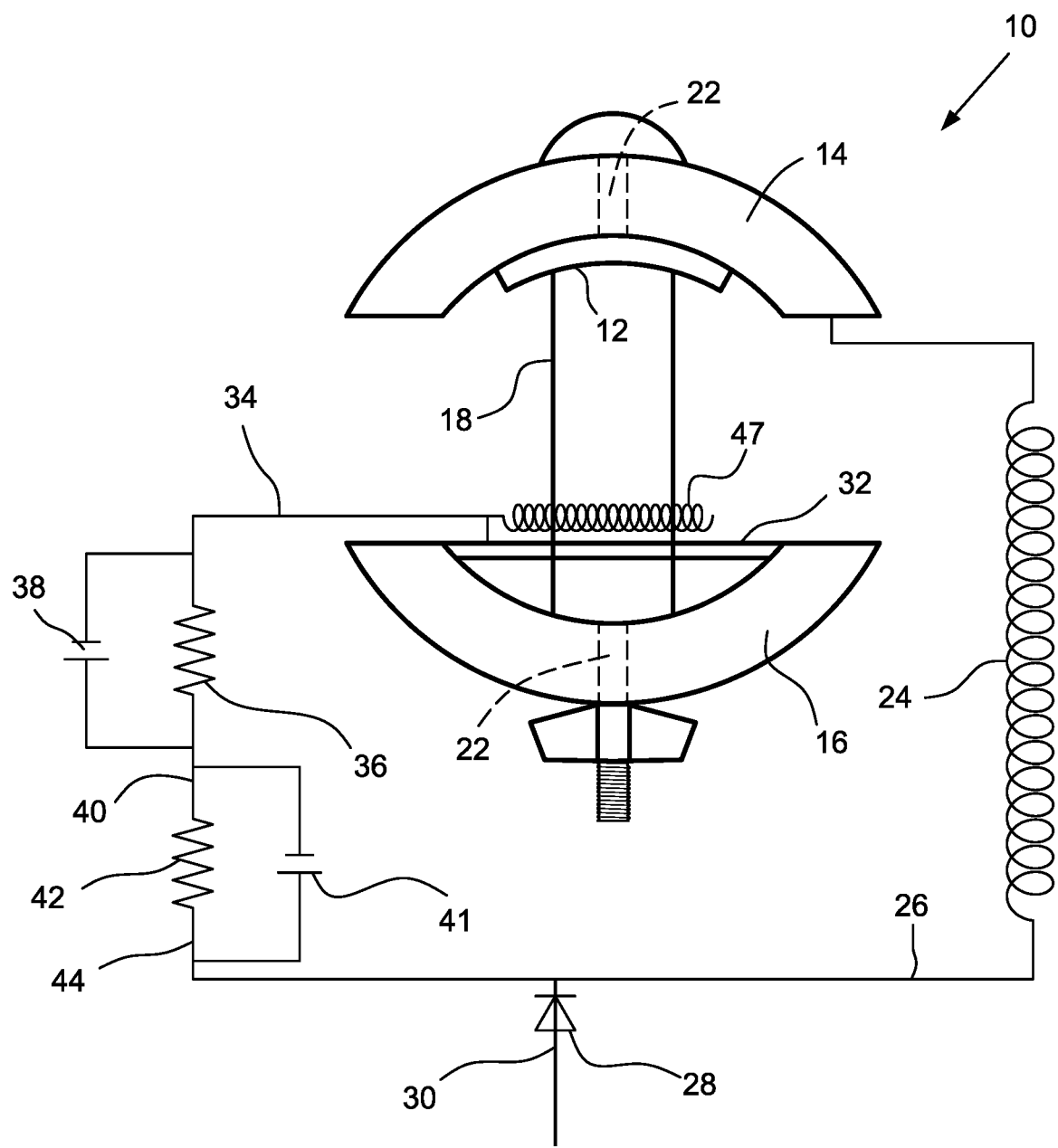
FIG. 1 is an end view of the analog matching filter arrangement.
Figure 2:
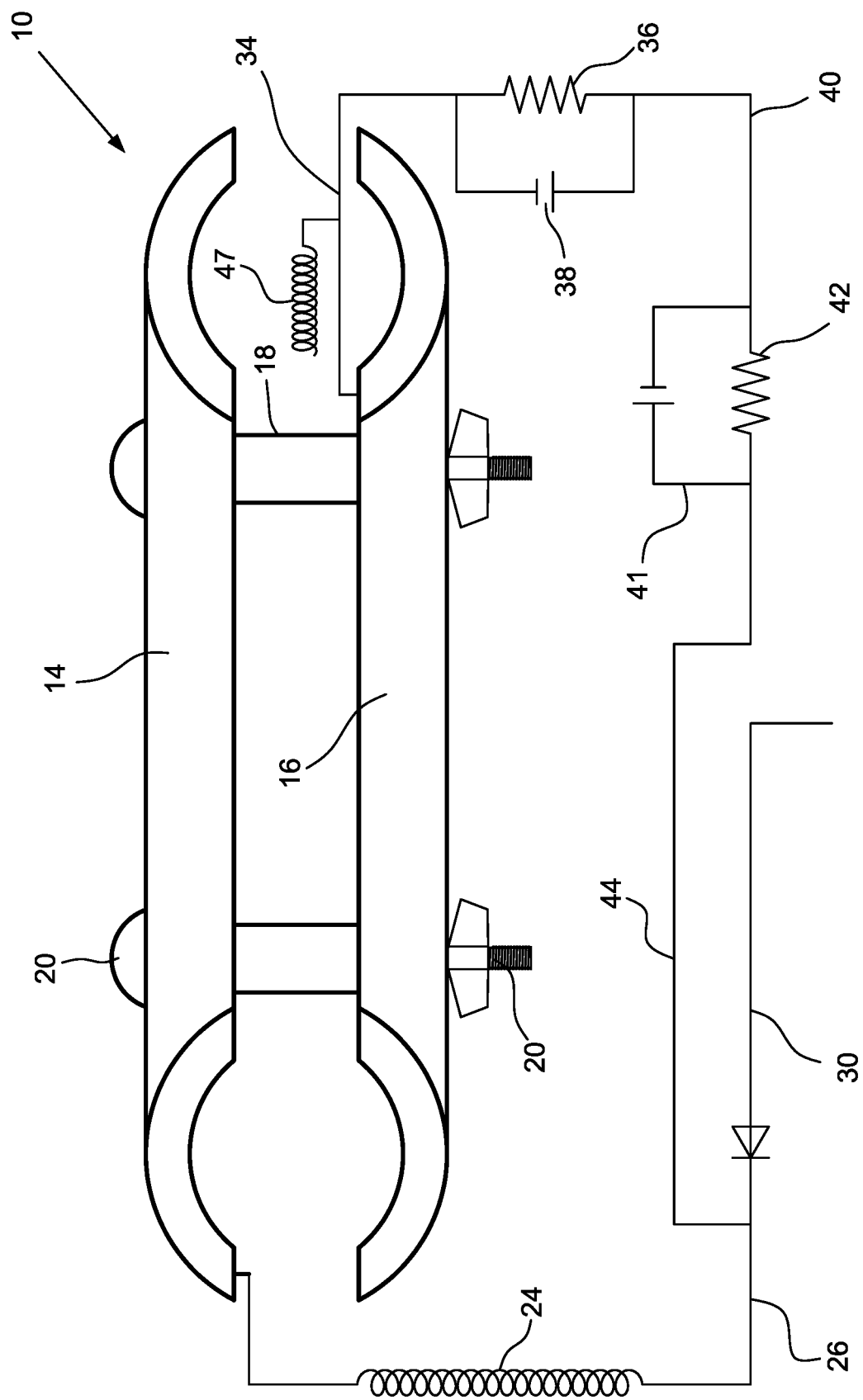
FIG. 2 is a side view.

The described embodiments relate to an analog matching filter formed of compositions of matter using initially neutral material chosen to be an exact dielectric replicate of an entity to be detected via dielectrokinesis (phoresis), which according to the described embodiments is smokeless gunpowder. The analog matching filter is an essential element in triggering and also maximizing both the mechanical torque and energy replenishment modes using dielectrokinesis (phoresis) methods to detect entities.

The filter action of this embodiment is specific for smokeless gunpowder and compositions containing smokeless gunpowder.

The dielectric replicate material comprising the analog matching filter functionally performs a spatial dielectric property matching between the entity of interest and a locator device to locate the entity, which is smokeless gunpowder according to the described embodiments. The filter enables the device to operate using the dielectrokinesis (phoresis) phenomena to specifically detect only those entities matching the dielectric response signature of the analog matching filter component. The dielectric signature includes both the dielectric constant and dielectric loss frequency spectra and all characteristic time constants controlling the polarization evolution/mechanics in external electric fields.

There are two primary elements for the dielectrokinesis entity location detection device to operate. The first element is an external electric field and spatial gradients thereof, and the second element is the selective dielectric analog matching filter of the described embodiments. As noted above, the external electric field and gradients thereof can be provided by the entity of interest itself as is the case when animate species or many inanimate entities are the entities of interest to be detected.

The analog matching filter of the described embodiments can be used with conventional electronic components (resistors, capacitors, inductors, transistors, etc.) in the overall operational design of the type of locator device used to detect the presence or absence of a specific entity of a predetermined type.

The external electric field and gradients thereof of the target entity defines a specific polarization pattern for the entity. In order to detect the target entity electric field and gradients thereof, it is necessary to impart an opposite polarization pattern on a detector element such as an antenna, dielectric collector or the like.

It has been discovered that specific combinations of materials provide the desired effects of the analog matching filter. FIG. 1 illustrates a filter 10 according to a first embodiment. As shown in FIG. 1, the filter 10 includes a replicate dielectric property matching material 12 within a spaced plate arrangement including a first plate 14 coupled with a second plate 16. According to the described embodiments, the replicate dielectric property matching material 12 is smokeless gunpowder. As shown, the plates 14, 16 may be curved along their longitudinal axes with concave surfaces facing each other. Alternatively, the plates 14, 16 may be parallel or constructed in different shapes. The pair of plates 14, 16 disposed enclosing the replicate dielectric property matching material 12 are held at a preferred distance by nylon spacers 18 secured via a suitable fastener 20. The plates 14, 16 may be formed by acrylonitrile-butadiene-styrene (ABS), for example, or other suitable polymers.

Each plate 14, 16 may be provided with a hole 22 at ends thereof or in each of the four corners of the plates. The plates 14, 16 are held at a set distance determined by the replicate material 12 by two to four of the spacers 18 through the holes 22. Each of the fasteners 20 passes through one of the holes 22 in the plates 14, 16, through the spacer 18, through the opposing hole 22 in the opposite plate 14, 16, and a nut is applied to the threaded section of the fastener 20 to secure the plate 14, 16 and the spacers 18. The fastener 20 may be any suitable material such as stainless steel or nylon.

The replicate material 12 is disposed on an interior surface of the first plate 14 via an adhesive or the like such as cyanoacrylate. The amount of adhesive may be minimized so that the surface of the replicate material 12 is exposed and not encased by the adhesive. The replicate material 12 functionally performs a spatial dielectric property matching.

A copper wire or a silver coated copper wire 24 is connected to the first plate 14. The connection may be made in any suitable manner, and in an exemplary embodiment, the connection is made by drilling a hole in the cross section of the first plate 14 that is slightly larger than the diameter of the silver coated wire 24. An adhesive such as cyanoacrylate may be used to connect the first plate 14 at the drilled hole to the end of the silver-plated copper wire 24. The end of the silver coated silver wire 24 is inserted into the drilled hole in the first plate 14. The length of the wire 24 may be nominally two inches. The silver coated copper wire 24 when selected in the embodiment serves to reduce impedance.

A first conductive wire 26 connects the silver coated copper wire 24 to a diode 28. The connections are made by solder or the like. A second conductive wire 30 connects the diode 28 to an internal member 46 of a detector element (described below).

A copper plate or sheet 32 is attached to an interior surface of the second plate 16 by an adhesive, such as cyanoacrylate. A copper wire 47 is connected to the copper plate by solder.

The copper wire increases the conductive surface area proximate to the replicate material. A third conductive wire 34 connects the copper plate 32 to a first resistor 36 and a first capacitor 38 in parallel. The connections may be made by solder or other suitable alternative. The first resistor 36 and the first capacitor 38 serve to produce a time constant less than 10 Hz.

A fourth conductive wire 40 connects the first resistor 36 and the first capacitor 38 to a second resistor 42 and a second capacitor 41 which are also in parallel. The connection may be made by solder or an alternative. The second resistor 42 and the second capacitor adjust the time constant less than 10 Hz.

A fifth conductive wire 44 connects the second resistor 42 in parallel with the capacitor 41 to the conductive wire 26 and then to the diode 28. The first plate 14 having the replicate material 12 attached is connected to the copper plate 32. The diode 28 is connected by the second conductive wire 30 to an internal member. The internal member reacts to currents in the conductive wires according to the principles of the described embodiments. The arrangement permittivity transmits (or "permits") an electric field to charge an analog matching filter, as described in the present application, and allows electric field charge to be stored and converted to a dielectrokinesis (phoresis) force. The selective permittivity is arranged in an analog matching filter in an RC circuit that enables the electric field stored charge to be converted to the dielectrokinesis (phoresis) force, thereby enabling the detection of an entity, which is smokeless gunpowder according to the described embodiments.

The values of the resistors, capacitors and diodes are determined by the replicate material selected. That is, these values will vary for different replicate materials.

Figure 3:
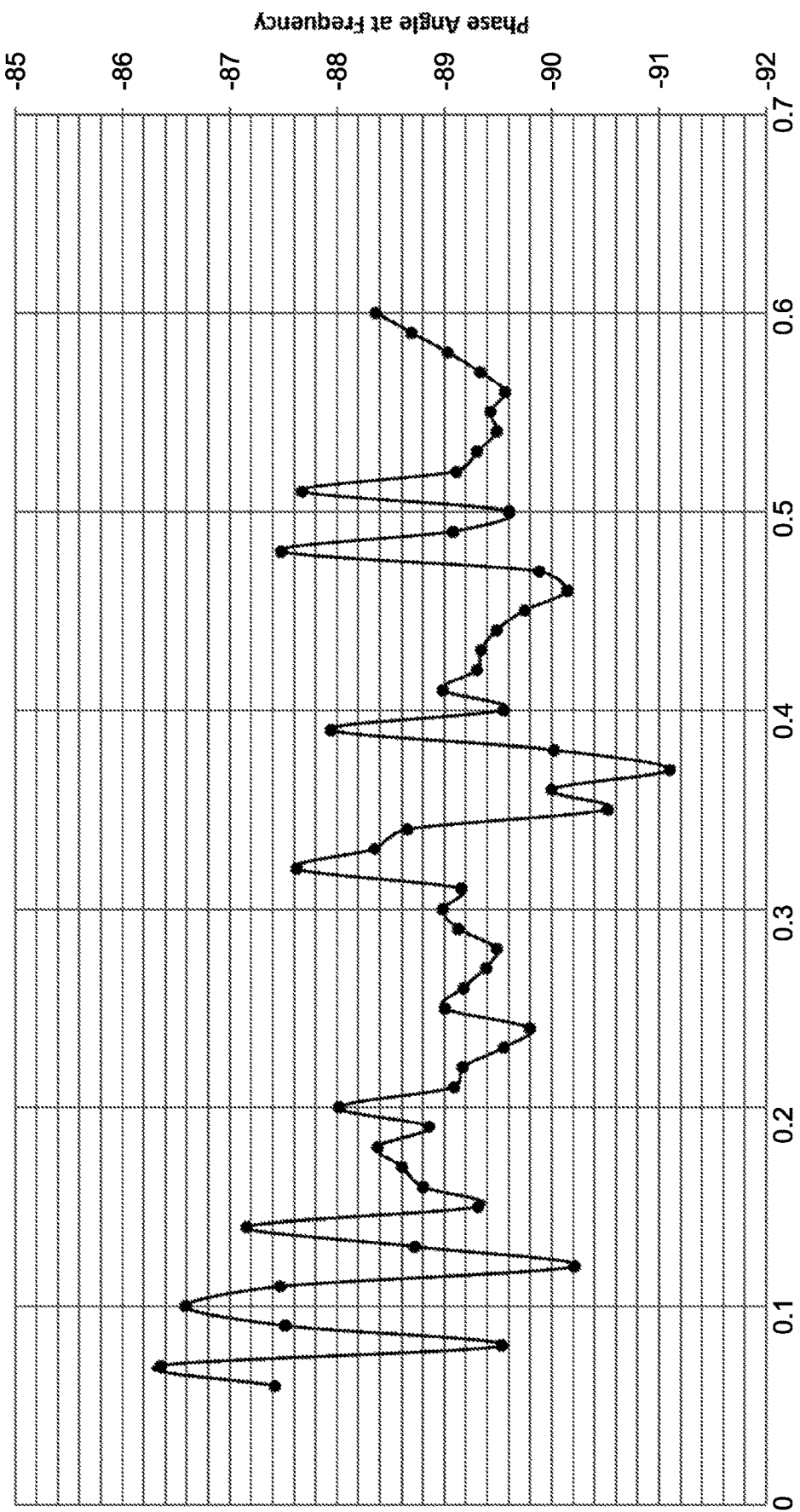
FIG. 3 is a chart showing electrical characteristics of the analog matching filter.

The analog matching filter is capacitively coupled to an enclosure 48 (see FIG. 4) of the detector element. In one embodiment of the analog matching filter, the permittivity of the analog matching filter is below 1 Hz. Above 1 Hz, the analog matching filter does not permit a charge to be stored. Below 1 Hz, the analog matching filter permits storage of a charge that is transmitted from the internal member through the conductive wires and RC component. The stored charge is then converted to the dielectrokinesis (phoresis) force on the internal member. With reference to FIG. 3 the phase shift indicates electron flow.

The replicate dielectric property matching material 12 is selected in accordance with the characteristics of the entity to be detected. That is, the replicate property matching material contains identical dielectric properties, time constants and related macroscopic friction coefficients to those of the entity material to be detected. In some embodiments, the replicate matching material is smokeless gunpowder including compositions of nitrated cellulose and nitroglycerin. Other replicate matching materials may be suitable.

Figure 4:
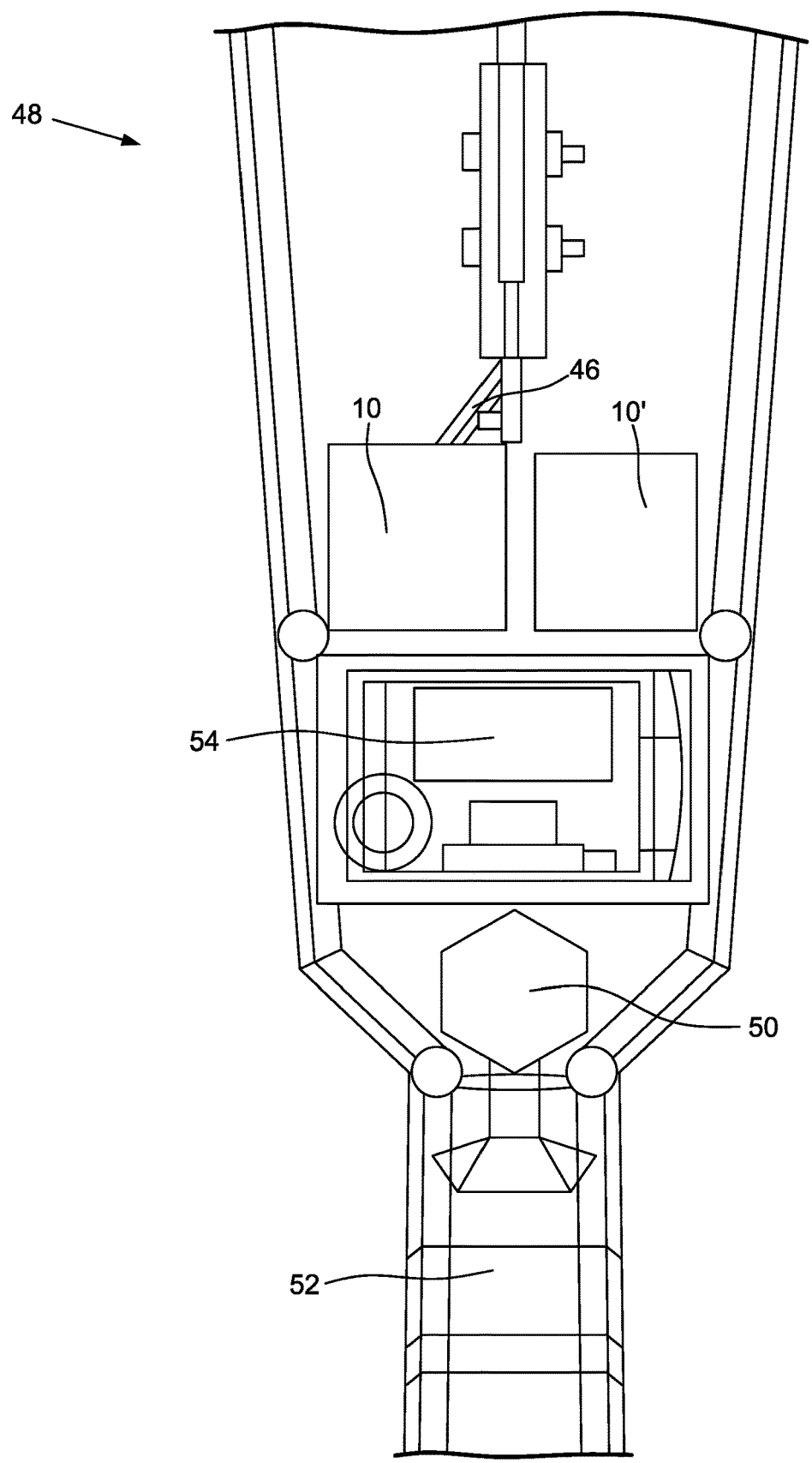
FIG. 4 shows an exemplary application of the analog matching filter in a sensor device.

With reference to FIG. 4, first and second analog matching filters 10, 10' may be placed within an enclosure 48 with suitable switching change via a selector switch 50 from one analog matching filter 10 (for smokeless gunpowder) to the other analog matching filter 10' (for a different entity or possibly a different type of smokeless gunpowder), each having a different replicate property matching material for a specific detection target. The switching may be designed to select single or multiple Analog Matching Filters and the associated replicate property material providing discrimination for triggering the dielectrokinesis (phoresis) force. The housing 48 includes a handle 52 and a sensor display 54 with suitable electronics and an internal member 46.

The dielectrokinesis (phoresis) phenomena can be used with the current analog matching filter 10 in at least two methodologies to enable the detection and location of specific entities of interest. The first methodology utilizes the dielectrokinesis (phoresis) force directly. This is usually observed via a torque "action at a distance" motion acting around a well-defined pivot point and line. An example of this application is described in commonly owned, U.S. Pat. No. 5,748,088, the disclosure of which is hereby incorporated by reference.

The second methodology is where an internal member has a fixed end and a freely moving end. In this second methodology the freely movable end of the internal member is moved via the dielectrokinesis (phoresis) force. The dielectrokinesis (phoresis) force acting on the internal member creates movement of the free end of the internal member. The dielectrokinesis (phoresis) force creates stress on the fixed end of the internal member. The dielectrokinesis (phoresis) force creates a stress along the longitudinal axis of the internal member. These stresses can be detected and used to drive an output display.

Static electrification proceeds via naturally-occurring contact charging (static or dynamic) which includes transfer of electrons, ions, and other charged chemical species as well as via the interfacial triboelectric charging. Static electrification also proceeds via artificially-occurring industrial processes used in manufacturing the smokeless gunpowder. The working hypothesis uses known static electrification effects as its basis. The spatial gradient effect is manifested where the high spatial gradient non-uniformity of the electric fields is largest, especially near the distribution's geometrical edge where the static electrification has not occurred, and the electric fields are near zero. This effect is also known as the "fringing electric field" effect.

The very high electrical resistivity of smokeless gunpowder does not allow the static electrification charges to leak harmlessly to ground. On the contrary, the charges are continuously accumulated in the interfaces and on the surface (bulk quantity) building up very high local electrical surface voltages in the tens of kilovolts. The static electrification charges on smokeless gunpowder are very long-lasting, with characteristic times for exponential decay of $10^2$ to $10^6$ seconds (days to months). This is generally referred to as near-DC frequency. The time constant depends on the inherent electrical resistivity of the smokeless gunpowder or other materials and the dielectric energy storage constant and dissipation loss describing smokeless gunpowder's electric polarization properties. The ever-present nature of static electrification ensures that the long-lasting static electrification electric field patterns have significant spatial gradients. The voltages and electric field patterns decrease as distance increases from the surface of the smokeless gunpowder. In addition, various inherent free- and bound-charge electron traps exist via surface chemistry effects on all materials, in particular high resistivity energetic materials including smokeless gunpowder. See Table 2. These traps form pre-charged under layers for electrons, ions, and other chemical species transferred via static electrification.

Materials such as smokeless gunpowder produce an electric field that is unique. Some examples of materials with unique dielectric constants are contained in Table 1. Smokeless gunpowder develops its own unique material-specific electric field spatial gradients. Smokeless gunpowder has a unique spatial gradient pattern from the combination of time-independent gradients from trapped ions/electrons and time-dependent gradients from triboelectric charging.

Smokeless gunpowder low resistivity predicts a time dependent changing electric field much lower than one Hz.

Electrical characteristics of the described analog matching filter were independently tested. The operational mode is an RC capacitive arrangement. The negative phase angle indicates that the current leads, voltage lags. See FIG. 3. The reactive range of the analog matching filter is in the frequency range below 1 Hz.

Discriminatory detection of the target electric field is achieved by the selective relative permittivity of the capacitive elements of the detection circuit.

The electric field of travel is optimized along the lateral interface of different dielectric constants. For example, the lateral interface of the air at 1.0 and ground at 3 to 6. The electric field is partially air propagating and partially local ground propagating depending upon the relative materials' input impedances.

The primary analytical technique used to characterize the dielectric polarization properties of smokeless gunpowder and other materials is dielectric spectroscopy. In this situation, we are interested in ULF frequency range (<30 Hz), where the stored electric energy and the dissipated electric energy are measured simultaneously.

Figure 5:
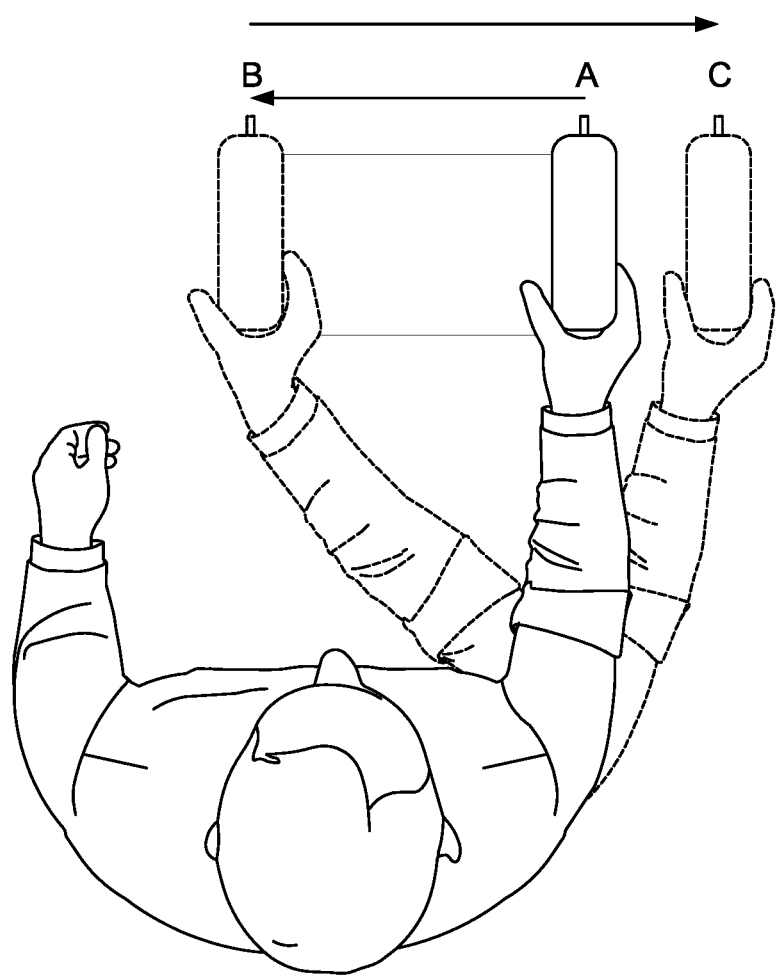
FIG. 5 shows a method of using the sensor device of FIG. 4 to detect the presence of smokeless gunpowder.

With reference to FIG. 5, the remote detection of smokeless gunpowder is performed by the following steps. Smokeless gunpowder is present within the range of the sensor. The operator moves the sensor from point A to point B and immediately moves the sensor from point B to point C. The movement between points A-B and B-C may be performed with the sensor maintained in essentially a horizontal orientation. The movements themselves may also be performed in an essentially horizontal plane. The movement of the sensor passes thru the unique electric field spatial gradients. The selective permittivity in the sensor's analog matching filter 10 in the RC circuit enables the unique electric field stored charge to be converted to the dielectrokinesis (phoresis) force and enables the detection of the smokeless gunpowder. That is, the selective permittivity via the replicate matching material enables the opposite polarization pattern carried by the electrical circuit to be converted to the dielectrokinesis (phoresis) force, thereby detecting the smokeless gunpowder.

The sensor's internal member 46 has a fixed end and a freely moving end. The freely movable end of the internal member 46 is moved via the dielectrokinesis (phoresis) force. The dielectrokinesis (phoresis) force acting on the internal member 46 creates movement of the free end of the internal member. The dielectrokinesis (phoresis) force creates stress on the fixed end of the internal member 46. The dielectrokinesis (phoresis) force creates a stress along the longitudinal axis of the internal member 46. These stresses can be detected and are used to drive the output display 54. One embodiment of the output display 54 has an area which displays the dielectrokinesis (phoresis) force produced by the internal member.

If the operator performs the movement A to B and B to C and the smokeless gunpowder is not present, no dielectrokinesis (phoresis) force is produced by the internal member 46. Without a stress on the internal member 46, a signal is not indicated on the output display 54. If the operator performs the movement A to B and B to C and the smokeless gunpowder is present, the dielectrokinesis (phoresis) force is produced by the internal member 46. In this instant, the unique smokeless gunpowder electric field stored charge is converted to the dielectrokinesis (phoresis) force. The dielectrokinesis (phoresis) force produces stress on the internal member 46. The stress on the internal member 46 is detected and indicated on the output display 54.

References supporting the described technological aspects are listed in Table 3.

TABLE 1

Dielectric Constant of Energetic materials and Common Materials (smokeless gunpowder contains compositions of nitrated cellulose with dielectric constants like Nitroglycerin)
Dielectric Constant < or = to 10 Hz

| | Substance |
|---|---|
| 7,000,000 To 50,000,000 | Human Tissue Range of value depending on which live organ tissue |
| 1,000 | Barium titanate ($BaTiO_3$) |
| 80 | Distilled Water |
| 70 | Seawater |
| 25 | TNT |
| 19 | Nitroglycerin |
| 3 to 11 | Carpet depending on material |
| 3 to 6 | Earth depending on location |
| 3 | Polyvinyl chloride (PVC) |
| 2.5 to 3 | Concrete depending on make up |
| 2.6 | Polystyrene (Styrofoam, packing peanuts, etc.) |
| 2.1 | Teflon (PTFE) |
| 1.00054 | Air |

TABLE 2

Properties of Explosives

| Material | Main Ingredient(s) | Resistance (ohms) | Resistivity (ohm-cm) Note 3 | Dielectric Strength - Static Breakdown (kV/mm) Note 4 |
|---|---|---|---|---|
| PBX-9404 | HMX | $2.8 \times 10^{10}$ | $4.19 \times 10^{10}$ | $29.0 \pm 1.8$ |
| PBX-9502 | TATB | | | $40.0 \pm 2.7$ |
| PBXW-108 | RDX | | | $21.7 \pm 3.1$ |
| Detasheet Type C | PETN | | | $16.1 \pm 0.6$ |
| Tetryl | | | | |
| PETN/TNT | | | | |
| Composition B | RDX + TNT | $2.4 \times 10^{10}$ | $3.59 \times 10^{10}$ | |
| TNT | | $6 \times 10^{10}$ | $8.97 \times 10^{10}$ | |
| PETN | | | | |
| RDX | | | | |
| HMX | | $2.8 \times 10^{10}$ | $4.19 \times 10^{10}$ | |
| Octol | TNT/HMX | $2 \times 10^{10}$ | $2.99 \times 10^{10}$ | |
| Baratol | TNT | $1.2 \times 10^{11}$ | $1.79 \times 10^{11}$ | |

TABLE 3

Technical References

1. P. E. Seeker, Static Electrification, University College North Wales, UK (1976).
2. D. J. Montgomery, Static Electrification of Solids, SS Physics, 9, p. 139 (1959).
3. W. R. Harper, Contact and Frictional Electrification, Oxford Press, UK (1967).
4. R. Cunningham, Static Electrification in Physics Encyclopedia, p. 891 (1974).
5. I. Inculet in Electrostatics and Applications, Chapter 5, Interscience (1973).
6. Excess Electrons in Dielectric Media, C. Ferradini (ed), CRC Press (1991).
7. Dielectric Spectroscopy of Polymeric Materials, J. P. Runt and J. J. Fitzgerald (Editors), Oxford University Press, London UK (2002).
8. Physics Encyclopedia (2nd Ed.), R. M. Besancon (Ed.), VanNostrand, NY (1974).

TABLE 3-continued

Technical References

9. Properties of Polymers: Estimation & Correlation with Chemical Structure, D. W. van Krevelen, Elsevier Publishing, The Netherlands (1976).
10. P. W. Cooper et al; Introduction to the Technology of Energetic materials, Horizon, John Wiley-VCH, London, UK (1997).
11. J. Yinon, Forensic and Environmental Detection of Energetic materials, John Wiley, London, UK (1999).
12. J. Yinon et al., Modem Methods and Applications in Analysis of Energetic materials, John Wiley, London, UK (1996).
13. Introduction to Polymer Science and Technology, H. S. Kaufman, J. J. Falcetta (Editors), Wiley-Interscience, NY (1977)
14. Textbook of Polymer Science (2nd Ed.), F. Billmeyer, Wiley-Interscience (1971)
15. Plastics for Electronics, M. T. Goosey (Editor), Elsevier NY (1985).
16. Physical Chemistry of Surfaces, A. W. Adamson, Interscience Publ. (1967).
17. R Schiller "Dielectric Relaxation", in Excess Electrons in Dielectric Media C. Ferradini (Editor) p 105 to 123, CRC Press, Boca Raton FL, USA (1991).
18. H. L. Friedman, J. Chem. Soc., Faraday Trans., 2, no. 79, p. 1465 (1983).
19. H. L. Freidman and D. Kivelson, J. Phys. Chem., 93, p. 7026 (1989).
20. R. Schiller, IEEE Transactions Electrical Insulation, 24, p 199 (1989).
21. Foundations of Electromagnetic Theory, J. Reitz et al., Addison-Wesley (1964).
22. U.S. Pat. No. 5,907,280 (issued May 25, 1999) assigned to DKL International, Inc.
23. U.S. Pat. No. 6,674,366 (issued Jan. 6, 2004) assigned to DKL International, Inc.
24. R. J. Lee, Static Dielectric Breakdown Strength of Condensed Heterogeneous High Energetic materials, NSWC, June 1987
25. E. E. Walbrecht, Dielectric Properties of Some Common High Energetic materials, Technical Memorandum 1170, Picatinny Arsenal, April 1963.
26. H. J. Jackson, A Study of the Electrical Characteristics of Some Energetic materials and Energetic material Mixtures, Technical Memorandum 1288, Picatinny Arsenal, October 1963
27. B. M. Dobratz, LLNL Energetic materials Handbook - Properties of Chemical Energetic materials and Energetic material Simulants, Lawrence Livermore National Laboratory, 16 Mar. 1981.
28. King, R. P., "Electromagnetic Surface Waves: New Formulas and Applications" in IEEE Transactions on Antenna and Propagation, 33, no. 11, p 1204 to 1212 (1985)
29. King, R. P. and Brown, M. F. "Lateral Electromagnetic Waves Along Plane Boundaries: A Summarizing Approach", Proceedings of the IEEE, 72, no. 5, p 595 to 611 (1984)

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. An analog matching filter comprising:
a first plate;
a second plate coupled with the first plate and separated from the first plate via a spacer;
a replicate matching material fixed to an inside surface of the first plate;
a conductive plate or sheet fixed to an inside surface of the second plate; and
an electrical circuit connecting the first plate to the conductive plate or sheet, wherein the replicate matching material and the conductive plate or sheet generate an opposite polarization pattern carried by the electrical circuit that is based on a polarization pattern of smokeless gunpowder according to a spatial gradient of the smokeless gunpowder local electric field distribution.

2. An analog matching filter according to claim 1, wherein the replicate material is configured to perform a spatial dielectric property matching of the smokeless gunpowder.

3. An analog matching filter according to claim 1, wherein the replicate matching material is selected in accordance with dielectric polarization characteristics of the smokeless gunpowder.

4. An analog matching filter according to claim 1, wherein the replicate matching material comprises one or more dielectric materials.

5. An analog matching filter according to claim 1, wherein the replicate matching material comprises smokeless gunpowder.

6. An analog matching filter according to claim 1, wherein the replicate matching material comprises identical dielectric properties, time constants and related macroscopic friction coefficients to those of the smokeless gunpowder.

7. An analog matching filter according to claim 1, wherein the replicate matching material comprises compositions of nitrated cellulose and nitroglycerin.

8. A sensor device for detecting smokeless gunpowder, the sensor device comprising:
a housing;
a first analog matching filter and a second analog matching filter, each of the first and second analog matching filters comprising:
a first plate,
a second plate coupled with the first plate and separated from the first plate via a spacer,
a replicate matching material fixed to an inside surface of the first plate,
a conductive plate or sheet fixed to an inside surface of the second plate, and
an electrical circuit connecting the first plate to the conductive plate or sheet;
an internal member that is configured to react to the opposite polarization pattern carried by the electrical circuit; and
a switch coupled with the first and second analog matching filters, the switch selectively activating the first analog matching filter or the second analog matching filter,
wherein the replicate matching material and the conductive plate or sheet in at least the first analog matching filter generates an opposite polarization pattern carried by the electrical circuit that is based on a polarization pattern of smokeless gunpowder according to a spatial gradient of the smokeless gunpowder local electric field distribution.

9. A sensor device according to claim 8, wherein the replicate matching material of the first analog matching filter is different from the replicate matching material of the second analog matching filter.

10. A sensor device according to claim 8, wherein the replicate matching material of the at least the first analog matching filter is selected in accordance with respective dielectric polarization characteristics of the smokeless gunpowder.

11. A sensor device according to claim 8, wherein the replicate material in the at least the first analog matching filter is configured to perform a spatial dielectric property matching of the smokeless gunpowder.

12. A sensor device according to claim 8, wherein the replicate matching material in at least the first analog matching filter is selected in accordance with dielectric polarization characteristics of the smokeless gunpowder.

13. A sensor device according to claim 8, wherein the replicate matching material in each of the first and second analog matching filters comprises one or more dielectric materials.

14. A sensor device according to claim 8, wherein the replicate matching material in at least the first analog matching filter comprises smokeless gunpowder.

15. A sensor device according to claim 8, wherein the replicate matching material in at least the first analog matching filter comprises identical dielectric properties, time constants and related macroscopic friction coefficients to those of the smokeless gunpowder.

16. A sensor device according to claim 8, wherein the replicate matching material in at least the first analog matching filter comprises compositions of nitrated cellulose and nitroglycerin.

17. A method of detecting smokeless gunpowder from a distance using a sensor including a first plate, a second plate coupled with the first plate and separated from the first plate via a spacer, a replicate matching material fixed to an inside surface of the first plate, a conductive plate or sheet fixed to an inside surface of the second plate, and an electrical circuit connecting the first plate to the conductive plate or sheet, wherein the replicate matching material and the conductive plate or sheet generate an opposite polarization pattern carried by the electrical circuit that is based on a polarization pattern of smokeless gunpowder according to a spatial gradient of the smokeless gunpowder local electric field distribution, the method comprising:

(a) moving the sensor in a first direction;

(b) immediately after step (a), moving the sensor in a second direction, opposite from the first direction, wherein steps (a) and (b) cause the sensor to pass through unique electric field spatial gradients of the smokeless gunpowder; and (c) using a selective permittivity via the replicate matching material to enable the opposite polarization pattern to be converted to a dielectrokinesis (phoresis) force based on a presence of the smokeless gunpowder.

18. A method according to claim 17, wherein steps (a) and (b) are practiced with the sensor in an essentially horizontal orientation.

19. A method according to claim 17, wherein steps (a) and (b) are practiced across an essentially horizontal plane.

20. A method according to claim 17, further comprising, after step (c), driving a display based on the dielectrokinesis (phoresis) force.

* * * * *